(12) United States Patent
Geltser (10) Patent No.: US 7,393,687 B2
(45) Date of Patent: Jul. 1, 2008

(54) BIOMIMETIC 3-DIMENSIONAL SCAFFOLD WITH METABOLIC STREAM SEPARATION FOR BIOARTIFICIAL LIVER DEVICE

(75) Inventor: Ilia Geltser, Houston, TX (US)

(73) Assignee: William Marsh Rice University, Houston, TX (US)

(*) Notice: Subject to any disclaimer, the term of this patent is extended or adjusted under 35 U.S.C. 154(b) by 149 days.

(21) Appl. No.: 11/184,290

(22) Filed: Jul. 18, 2005

(65) Prior Publication Data

US 2006/0035376 A1  Feb. 16, 2006

Related U.S. Application Data

(60) Provisional application No. 60/588,580, filed on Jul. 16, 2004.

(51) Int. Cl.
*C12N 5/00* (2006.01)
*C12N 5/06* (2006.01)
(52) U.S. Cl. .................. 435/402; 435/325; 435/373; 435/395; 435/401
(58) Field of Classification Search .................. None
See application file for complete search history.

(56) References Cited

U.S. PATENT DOCUMENTS

| | | |
|---|---|---|
| 3,734,851 A | 5/1973 | Matsumura |
| 4,963,489 A | 10/1990 | Naughton et al. |
| 5,510,254 A | 4/1996 | Naughton et al. |
| 5,605,835 A | 2/1997 | Hu et al. |
| 6,863,551 B2 | 1/1999 | Woerly |
| 6,008,049 A | 12/1999 | Naughton et al. |
| 6,133,030 A | 10/2000 | Bhatia et al. |
| 6,140,039 A | 10/2000 | Naughton et al. |
| 6,218,182 B1 | 4/2001 | Naughton et al. |
| 6,372,495 B1 | 4/2002 | Flendrig |
| 2003/0017142 A1 | 1/2003 | Toner et al. |

FOREIGN PATENT DOCUMENTS

WO   WO 97/12960   *   4/1997

\* cited by examiner

*Primary Examiner*—Daniel M Sullivan
(74) *Attorney, Agent, or Firm*—Conley Rose, P.C.; Rodney B. Carroll (57) ABSTRACT

A bio-artificial organ comprises a substrate comprising a roll of a substrate material, and a plurality of cells adhered to the substrate, the roll being formed from a sheet rolled to form a plurality of layers that include spacers and spaced openings such that at least a first set of parallel chambers is formed when the roll is formed, the chambers being manifolded to a first inlet and a first outlet. The bio-artificial organ may further include at least a second chamber, the second chamber being isolated from the first set of chambers by at least a cell barrier. A method for assembling a bio-artificial organ comprises a) providing a substrate for cell culture capable of forming a roll, the substrate having a surface, b) patterning the surface of the substrate, c) seeding cells onto the substrate, and d) reeling the substrate into a cylindrical roll.

17 Claims, 7 Drawing Sheets

BIOMIMETIC 3-DIMENSIONAL SCAFFOLD WITH METABOLIC STREAM SEPARATION FOR BIOARTIFICIAL LIVER DEVICE

CROSS-REFERENCE TO RELATED APPLICATIONS

This application claims benefit of U.S. application Ser. No 60/588,580, filed Jul. 16, 2004, and entitled "Biomimetic 3-Dimensional Scaffold With Metabolic Stream Separation For Bioartificial Liver Device," which is incorporated herein by reference in its entirety.

STATEMENT REGARDING FEDERALLY SPONSORED RESEARCH OR DEVELOPMENT

Not Applicable.

FIELD OF THE INVENTION

The present invention relates generally to a bimimetic liver and method for constructing same.

BACKGROUND OF THE INVENTION

Liver failure is the seventh leading cause of death in the USA, with 300,000 hospital admissions per year and more than 40,000 deaths. Liver failures are classified as acute or chronic. A common type of acute liver failure is Fulminant Liver Failure (FLF), defined as severe impairment of hepatic functions in the absence of pre-existing liver disease. The common FLF causes include viral hepatitis, poisoning, and stroke. Common types of chronic liver failure include viral or alcohol cirrhosis, drug and toxin induced diseases.

Spontaneous self-regeneration of liver occurs in about 25% of FLF patients (which is not always possible to predict) and in a very small percentage of chronic liver patients. The most common and often the only treatment option for liver failure is a liver transplant, at a typical cost of about $400,000 per transplant in the USA, making it a $2 billion industry in the USA alone. About 5,000 transplants are available in the USA per year, but there are 17,000 potential recipients on the waiting list. The organ shortage is expected to increase as the incidence of viral hepatitis type C (HVC) is continues to increase. One of the driving forces are the 4 million Americans currently infected with HVC, 15% of these are expected to require a transplant. The total number of chronic liver failures is projected to triple between 2002 and 2010.

There has been intensive research into cell-containing liver-assist devices (LADs) for over 20 years and several devices have achieved clinical trials. In FLF treatment, LADs promise the patients a temporary relief of liver metabolic load and a chance for the liver to regenerate itself. In this case, LADs prevent wastage of a donor organ. In chronic liver failure treatment, LADs promise a bridge to transplant, and, potentially a long term support option.

However, none of the cell-containing LADs has successfully passed all clinical trials and achieved an FDA approval. The main problem is the poor long-term device performance due to a low viability and a loss of differentiated function of hepatocytes. A second problem is the lack of biliary excretion. A third problem is a limited device performance, even when the hepatocytes are still functional, due to non-uniform cell distribution and non-uniform flow distribution. A fourth problem is a low cell density, resulting in a need for a relatively large device size. Advantages and drawbacks of prior art are detailed in the following paragraphs.

The hollow fiber design was the earliest design concept and has advanced farthest through clinical trials. The cells are attached inside the fibers, possibly trapped in a gel, or outside the fibers. The blood or other nutrient-containing medium is perfused to the opposite side of the fiber. The assembly and manifolding of several thousand of these hollow fibers into a bioreactor is a complex and slow process. Cells are perfused after the device assembly. Cell density has been relatively low. Additionally, attempts to culture different cell types in the fibers have proven unsuccessful. Because of low cell density and the difficulty of assembling thousands of hollow fibers, long fibers tend to be used, resulting in non-uniform conditions along the fiber length. An attempt at supplying different medias through several sets of hollow fibers resulted in very complex geometry, and limited scale-up to about 2.5% of physiological human liver cell numbers.

The perfused bed scaffolds typically comprise three dimensional open pore architectures. These scaffolds are easy to scale up, can be shaped with rapid prototyping tools with a narrow pore distribution in a target range. Pore sizes can be adjusted to promote high cell density and vascularization. However, in LAD applications, these scaffold designs have several drawbacks, including residual chemicals, no provision for separation of metabolic flows, and no provision for patterning different cell types in target geometries, non-uniform perfusion, clogging, and exposure to shear.

The encapsulated cell suspension design offers the ease of scale-up and a uniform microenvironment. The drawbacks include poor cell stability and loss of differentiated function (particularly, for hepatocytes, which are attachment-dependent cells), barriers to nutrient transport due to encapsulation, degradation of capsules over time and exposure of cells to shear forces.

The flat plate design is another known device. In this method, it is possible to achieve uniform cell distribution and microenvironment. Multiple patents have recognized the advantage of multilayer arrangements, where cells can be sandwiched between collagen or biologically derived matrices (basal lamina, Matrigel) and oxygen permeable membranes, such as U.S. Pat. Nos. 3,734,851 and 5,605,835. Several groups have verified modulation of hepatocyte polarity and formation of canaliculi. U.S. Pat. No. 5,605,835 shows an example of multilayer arrangement, stacked up to 50 layers and up to 200 layers and individually piped. In order to provide mechanical strength during assembly, the individual plates have to be relatively thick. The disadvantages of this design include exposure of cells to shear, low surface to volume ratio, low cell density, and complex scale-up.

A further improvement to flat bed design came from co-culturing layers of stromal cells with hepatocytes, which was demonstrated to increase viability and differentiated function of hepatocytes (U.S. Pat. Nos. 4,963,489; 5,510,254; 5,863,551; 6,008,049; 6,140,039; and 6,218,182). Further improvement came from separation of cells from oxygen containing medium by a membrane (U.S. patent application Ser. No. 200300017142), which allowed increased oxygenation without exposing cells to damaging flow shear stresses.

In order to create multilayer structures, it has been suggested to roll the substrate into a cylinder. In U.S. Pat. No. 6,218,182 two media, with different concentrations of solutes, flow on the ID and OD of the rolled-up cylinder. The purpose of such assembly is to create a diffusion gradient in the radial direction, which is believed to be beneficial for cell polarization and growth. The substrate may contain layers of multiple materials and different cell types. The products have to diffuse through multiple layers to reach and be removed by one of the media. The overall setup is geared to tissue growth rather than tissue function. The diffusion pathways are long (from ID to OD) and there is no provision for patterns within the layers or separation of various metabolic products.

In U.S. Pat. No. 6,372,495, hollow fibers are randomly embedded or attached to a porous sheet or mat. The fibers are minimum 100 microns OD and are arranged in parallel. The mat is 50 to 2000 microns thick (typically, about 500 microns) by 10-100 cm wide, and has 10-100 micron pores. The fibers are intended to serve as spacers during rolling-up the sheets, provide solid support for the sheets and exchange oxygen and carbon dioxide. After the roll-up, individual fibers (typically, 500 to 5000) are manifolded together and connected to a gas source, while space between the fibers is connected to liquid flow. After assembly, the porous media are infused with cells. Cells are protected from shear stresses by being embedded into the porous sheet. The invention has several drawbacks as discussed earlier: it is difficult to manifold several thousands of fibers, different cell types are not geometrically organized, and the diffusion path is longer than in a live liver. Also, metabolic products of the cells stay in the circulating liquid, and may, eventually, negatively affect the cell viability and differentiation.

Hence it remains desirable to provide a biomimetic liver that avoids the drawbacks of the prior art.

SUMMARY OF THE INVENTION

The present invention features a scaffold with a high degree of a 3-dimensional resolution and structure and combines it with targeted cell placement. The prior art accomplishes one or the other, but not both at the same time. The invention provides large cell attachment surface, a uniform 3-dimensional distribution of multiple cell types, a uniform media flow distribution with short diffusion pathways, and protection of hepatocytes from shear forces. The specific problems solved by current invention, means for solving them, and the benefits or the present invention are detailed below.

The present invention integrates a manifold into a rolled up cylinder. Inlet and outlet channels are formed by openings in the sheet. More specifically, the flat sheet is provided with a plurality of openings therethough. The openings are preferably but not necessarily formed close to the long edges of the flat sheet and are spaced such that when the sheet is rolled up the openings in successive layers align. The degree of alignment can be predetermined. When the sheet is completely rolled, the aligned openings form at least one channel extending from the outside to the center of the roll. If desired, multiple channels can be provided and it is not necessary that each channel extend all the way to the center of the roll. The sheet may optionally be rolled around at mandrel, which may then be removed, leaving an open central bore along the axis of the roll.

Thus, the present invention comprises a combination of features and advantages that enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENTS

Figure 1:
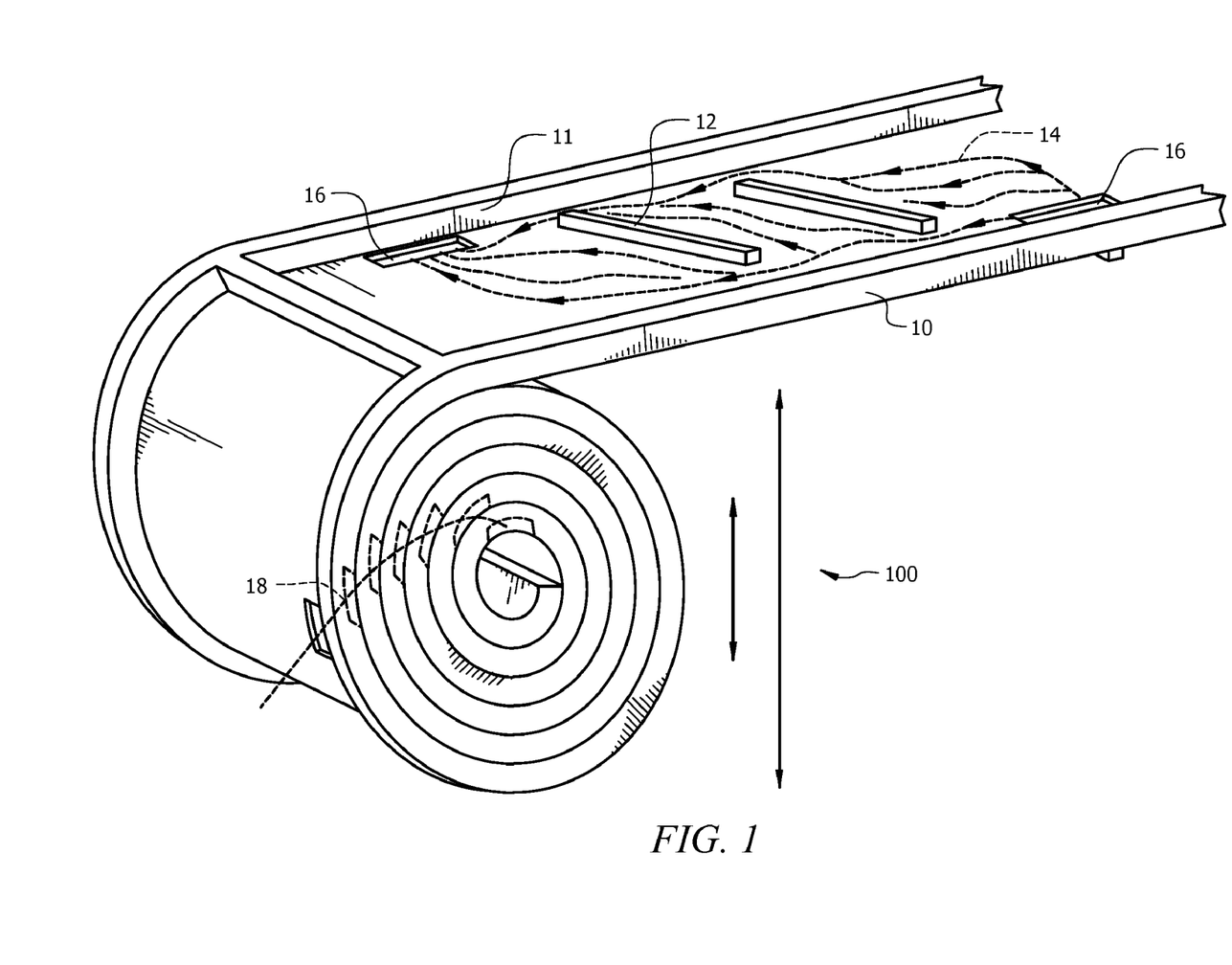
FIG. 1 is a schematic drawing of a multi-layer sheet constructed in accordance with the present invention.

A flat sheet of material can be patterned to direct a flow of fluid or gas media within the two in-plane directions. Assembling or stacking multiple sheets in a third dimension is often required when a larger surface area is desirable. In this case, an external pattern is required in order to direct media to every sheet. If the material is flexible enough, it can be rolled into a cylinder as shown in FIG. 1. As illustrated, a roll 100 is formed from a sheet 10 having at least one of its surfaces a pattern of side walls 11 and dividers 12 that produce a flow pattern 14. Openings 16 in the sheet allow fluid to pass between the layers in the roll. There are two approaches to supplying media to the cells. In the first approach, the media is supplied to the OD and is transported primarily in a radial direction, towards the ID. In the second approach, media is supplied to one end of the cylinder and transported longitudinally. The inlet and the outlet manifolds are external to the cylinder and are attached separately.

In a preferred embodiment, the present invention integrates a manifold into a rolled up cylinder. Inlet and outlet channels for each layer are formed by openings 16 in the sheet. More specifically, the flat sheet is provided with a plurality of openings therethough. Openings 16 are preferably but not necessarily formed close to the long edges of the flat sheet and are spaced such that when the sheet is rolled up the openings in successive layers align or almost align. The degree of alignment can be predetermined. When the sheet is completely rolled, the aligned openings form at least one radial channel 18 extending from the outside to the center of the roll. If desired, multiple channels can be provided and it is not necessary that each channel extend all the way to the center of the roll. The sheet may optionally be rolled around at mandrel, which may then be removed, leaving an open central bore along the axis of the roll.

In certain embodiments, each layer includes spacers or dividers 12 such that the overall thickness of a layer is greater than that of the sheet itself. The spacers 12 are preferably placed at least along the long edges of the sheet. The spacers may be formed integrally with the sheet, attached after the sheet is formed, or applied in the course of rolling process. Inclusion of the spacers results in a space being defined between adjacent layers, with the width of the space being equal to the height of the spacers. If desired, the space can be divided into chambers by including dividers equal to the height of the spacers. The dividers preferably extend fully or partially across the width of the sheet and are positioned such that when the sheet is rolled up the chambers defined by the spacers are each in fluid communication with at least one inlet and at least one outlet.

Figure 6:
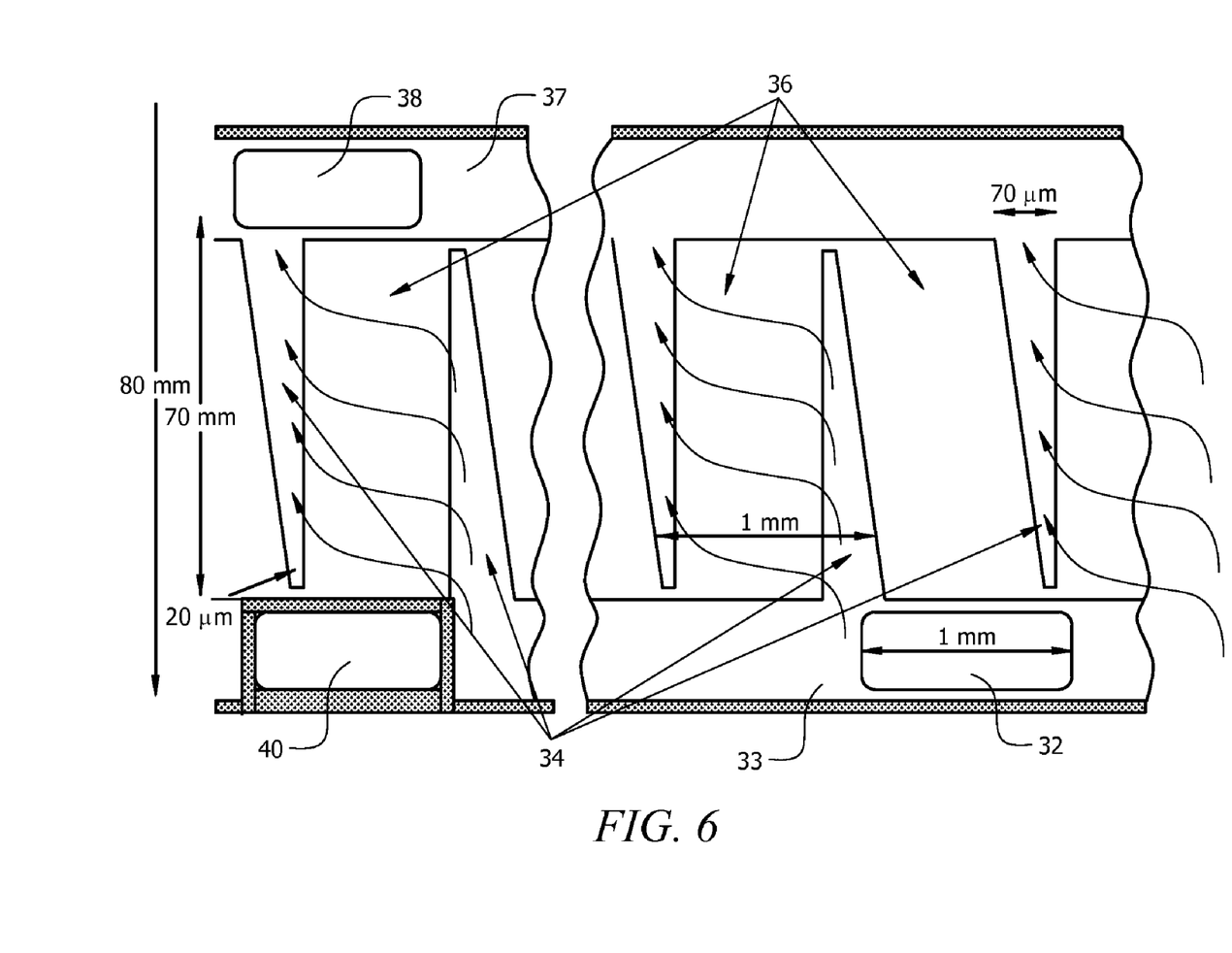
FIG. 6 is a simplified enlarged schematic view of a portion of a sheet constructed in accordance with another embodiment of the invention.

In certain embodiments, openings 16 are placed periodically with period P along the length of the sheet (FIG. 6). For a constant P value, and opening length L, if the layer thickness T is such that:

$$2*\pi*T \ll L \ll P$$

then the openings will stack nearly perfectly over each other as the sheet is being reeled or rolled up. Each channel formed by the aligned openings will form a manifold across the flat end of the cylinder, allowing distribution of a fluid across all of the layers and thereby allowing a three-dimensional media flow over large surface area. If P is made variable along the length of the sheet, the above relationship no longer needs to be satisfied to properly stack the channel openings.

Figure 2:
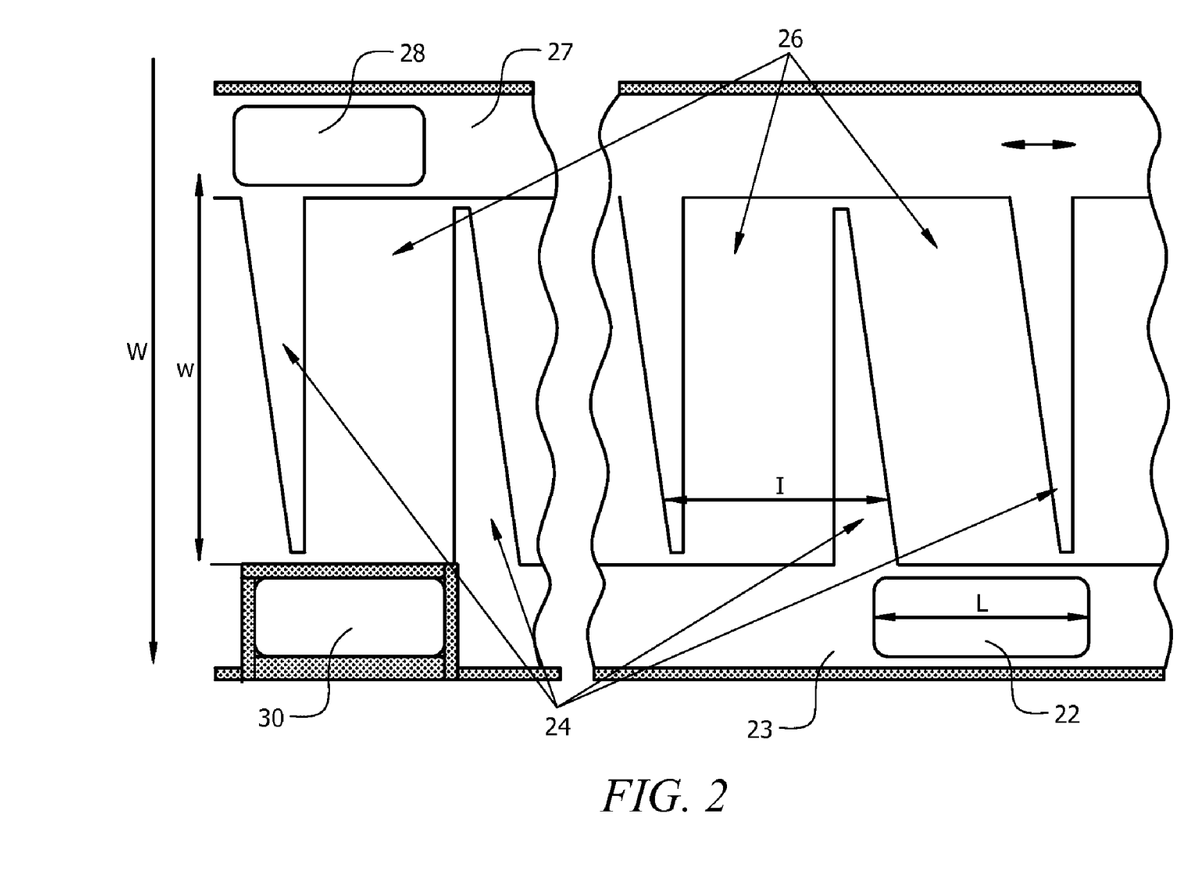
FIG. 2 is a simplified enlarged schematic view of a portion of a sheet constructed in accordance with a preferred embodiment of the invention.

This concept can be applied to devices that include two or more layers. In the two-layer example shown in FIG. 2, each unit of length of the rolled layers includes an inlet opening 22, a distribution manifold 23, a plurality of flow channels 24, a plurality of flow surfaces 26, a collection manifold 27, an outlet opening 28, and a separate flow channel 30 in fluid isolation from the rest of the same layer. Each layer further includes spacers that have a height such that the overall thickness of a layer is greater than that of the sheet itself. In the preferred embodiment shown, the spacers include the walls surrounding selected openings. The walls are preferably the same height as the spacers and have the effect of preventing fluid flow between the channel and the chamber defined at that layer. The channels preferably open at alternate layers, much like elevators that stop at either even or odd floors. Thus, independent media flows can be achieved in multiple layers wound into a compact cylindrical shape. Additional in-plane ridges and grooves may be patterned within the layers to achieve target flow pattern.

One primary application for the invention is as a scaffold for a cell-based Extra or Intra-corporeal Liver Assist Device (LAD), also known as a Bioartificial Liver.

Target Biological Structure

Figure 3:
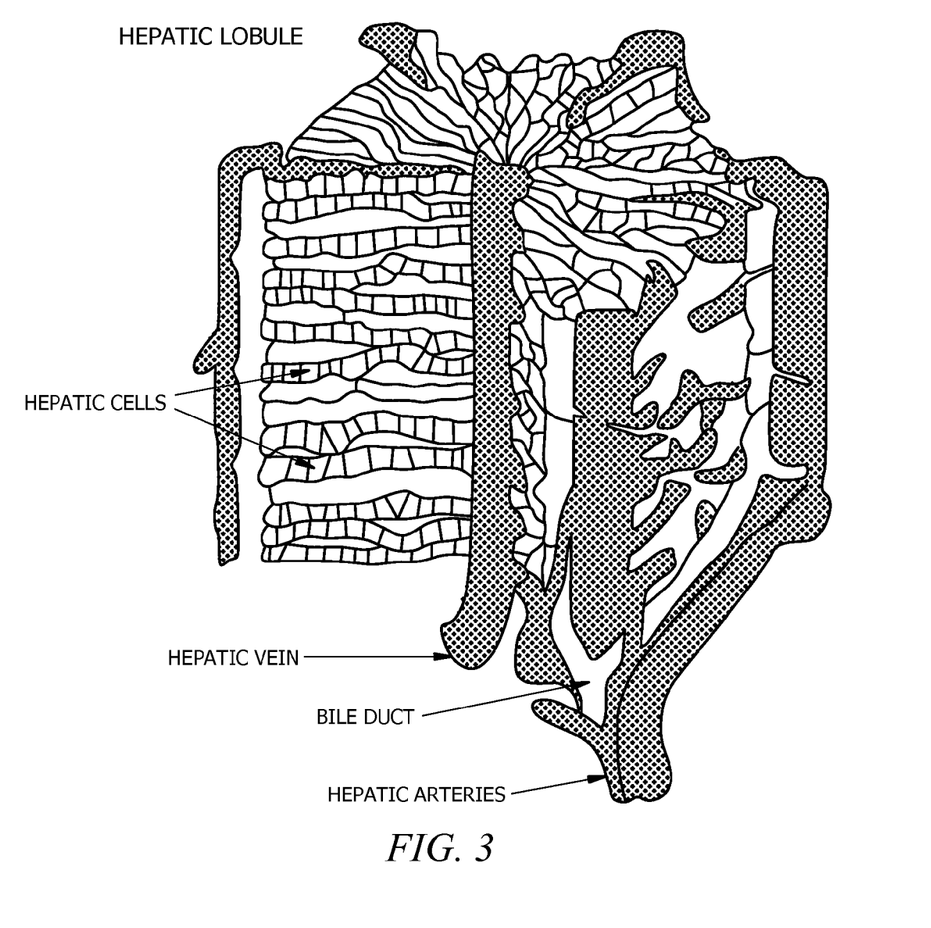
FIGS. 3 and 4 are schematic views of a liver.

The invention attempts to mimic the cell arrangement and flow pattern of the repeating subunit of the liver, a hepatic lobule, which is described below and shown in FIGS. 3 and 4. This lobule is a polyhedron, about 6 mm tall by 1 mm diameter, centered around the central vein. The portal vein, hepatic artery, hepatic bile duct and lymph vessels form interlobular vessels, known as the portal triad. Three or four portal triads border each hepatic lobule. The hepatic lobule is formed by plates of hepatocytes radiating from the central vein (FIG. 3). The plates are a single cell in thickness and appear as cords of cells when viewed edge-on. They are separated by the sinusoids and the perisinusoidal space of Disse.

Figure 4:
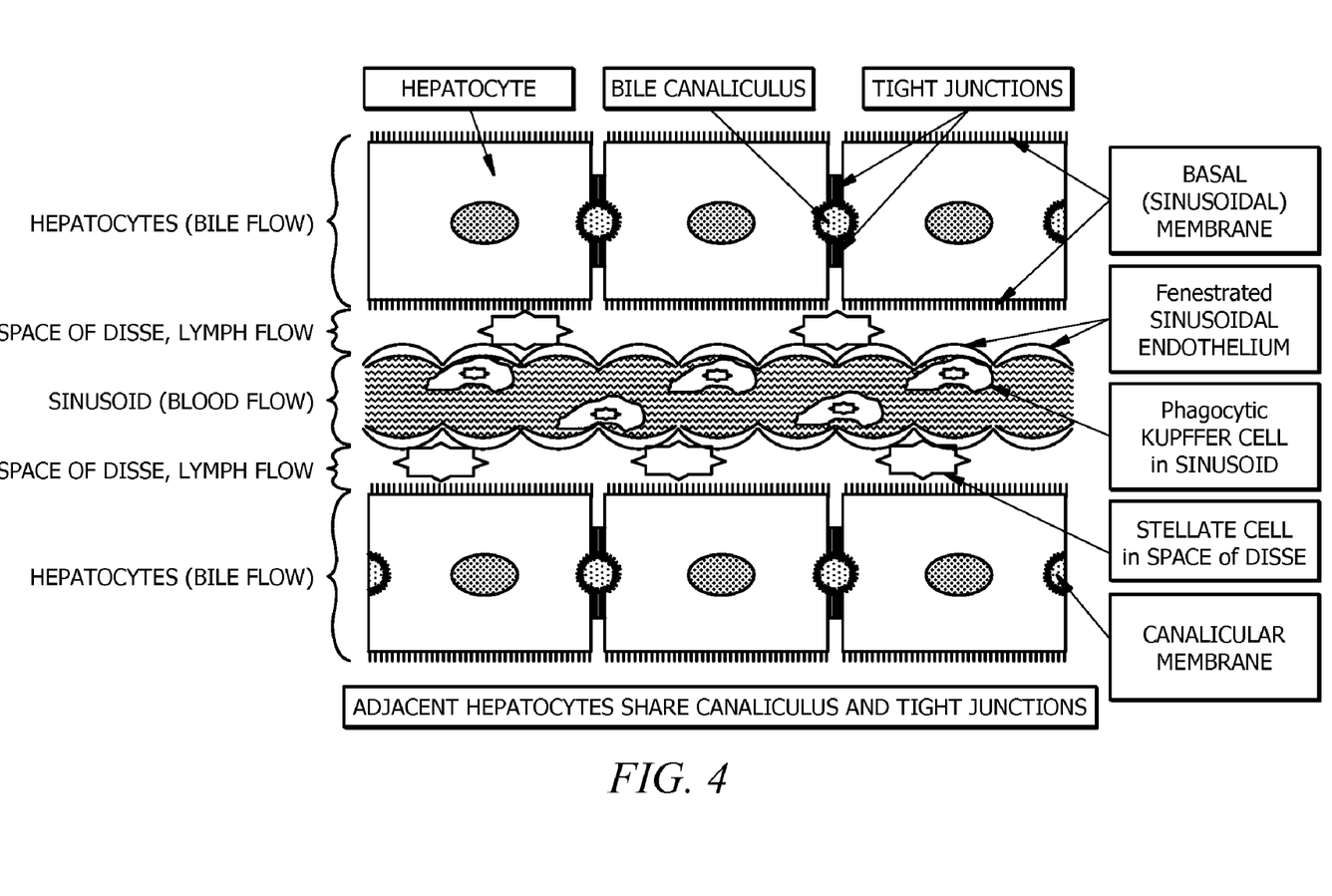

The sinusoids, about 10 μm in cross-section, are shown in the center of FIG. 4. The sinusoid walls are lined with endothelial cells like any blood vessel, but without the basal lamina. The gaps (fenestrations) between the endothelial cells result in a very porous structure. The endothelial cells confine blood cells to the sinusoids but allow access of plasma to the space of Disse and contact of plasma with hepatocytes. In addition to endothelial cells, the sinusoids are lined by phagocytic cells known as Kuppfer cells, fat storage cells known as Ito cells and by other cells. Collectively, liver cells other than hepatocytes are known as stromal cells.

The bile vessels begin as micron scale canaliculi formed by the plasma membranes and tight junctions of the adjacent hepatocytes. The bile canaliculi form networks within the lobule and coalesce at the periphery to form intralobular ductules that open into the bile ducts. The bile flows opposite to the blood.

The lymph vessels begin as exceptionally porous, micron scale capillaries in the space of Disse. The lymph vessels drain the excess fluid from the sinusoidal space through the large fenestrations in the endothelial lining. The lymph flows opposite to the blood.

Biomimetic Embodiment.

In a preferred embodiment, the present LAD aims to replace 10 to 30% of the normal liver function. Assuming a normal liver weight of 2.5 lbs with about $10^{11}$ cells, of which 85% are hepatocytes, a desired LAD should contain approximately $2 \times 10^{10}$ hepatocytes occupying an of area about 7-10 square meters on a substrate about 100 meters long. The LAD will preferably weigh about 0.5 lbs, have about 700 layers rolled into a cylinder with diameter about 80-100 mm and width about 70-100 mm. The outlet and inlet channels on the outer diameter are joined with suitable biocompatible tubes, which are connected to the target vessels in the body.

Figure 5:
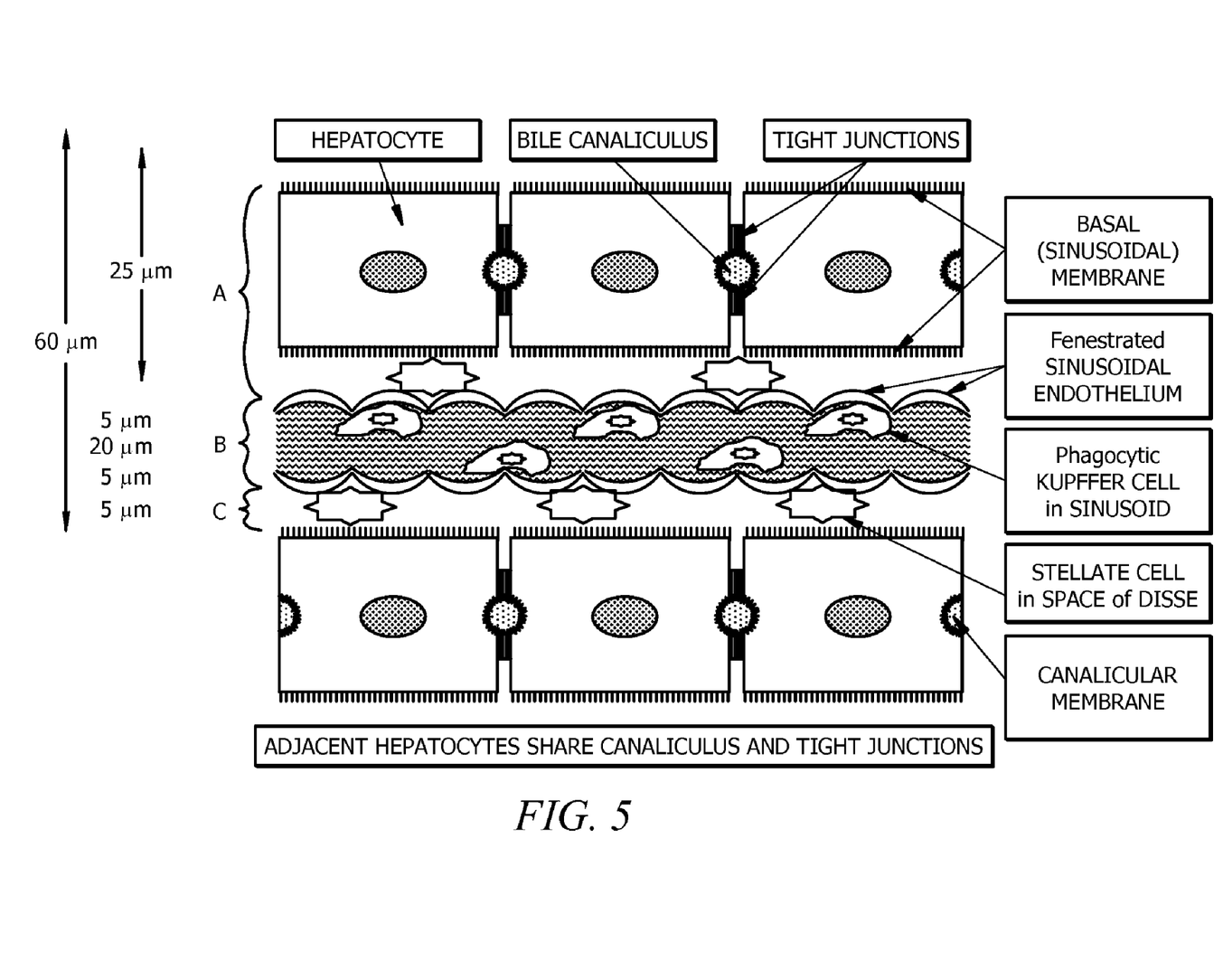
FIG. 5 is a schematic view of a liver constructed using the principles of the present invention.

The scaffold may have several layers each made with different materials and different patterns. For illustration, three scaffold layers and layer thicknesses are shown in FIG. 5.

In one embodiment, layer A has an intricate top side pattern. It supports and compartmentalizes hepatocytes during the assembly, provides attachment sites for hepatocytes, provides a porous spacer to create the Space of Disse, delineates the space where bile and is produced, and provides a drainage pattern. The layer is about 5 μm thick with 20 μm tall spacer ridges for hepatocyte separation. The central portion of the layer contains biodegradable material, such as porous Type I collagen, often used for hepatocyte culture or biodegradable polymer grafted with integrin receptor chains. The side areas of layer A are responsible for bile drainage, and are preferably made from a biodegradable material such as PDMS or silicone.

Layer B includes inlet opening 32, distribution manifold 33, blood flow channels 34, porous areas 36 for leakage into the space of Disc, collection manifold 37, blood outlet 38 and a separate bile flow channel 40 for blood supply, as shown in FIG. 6. It is preferably assembled from a flat sheet with imprinted blood flow channels and overlaid with a thin layer of the same material. This layer supports endothelial and Kuppfer cells during the assembly, provides porous transport from blood to endothelial cells, delineates channels for blood flow, and prevents blood channels from collapsing. The total thickness of layer B is preferably about 10-30 μm and more preferably about 20 μm. The layer is preferably made of a non-biodegradable material such as PDMS or silicone.

Layer C, although appearing similar to layer A, has only reduced functions of supporting endothelial cells and providing a porous spacer to create the space of Disse. Layer C is preferably ~5 μm thick, non-patterned, and manufactured from biodegradable material, similar to the central portion of layer A. The fluid flowing across layer C exits through openings that are fluidly isolated from adjacent layers, such as opening 40 in layer B.

For all of the layers, the biodegradable polymer can be chosen from a wide variety of FDA approved materials, including PLLA, PLGA, and novel polymers disclosed in prior art, including biodegradable UV-curable poly (caprolactone). The scaffold material may be further grafted with cell attachment factors, including fibronectine and hyaluronic acid or coated to resist or encourage protein and cellular adsorption.

This invention can be used to provide scaffolds for any of the common cell types, including, but not limited to patient autologous cells, allogenic donor cells, immortalized cell lines and xenogenic cells.

Assembly

Figure 7:
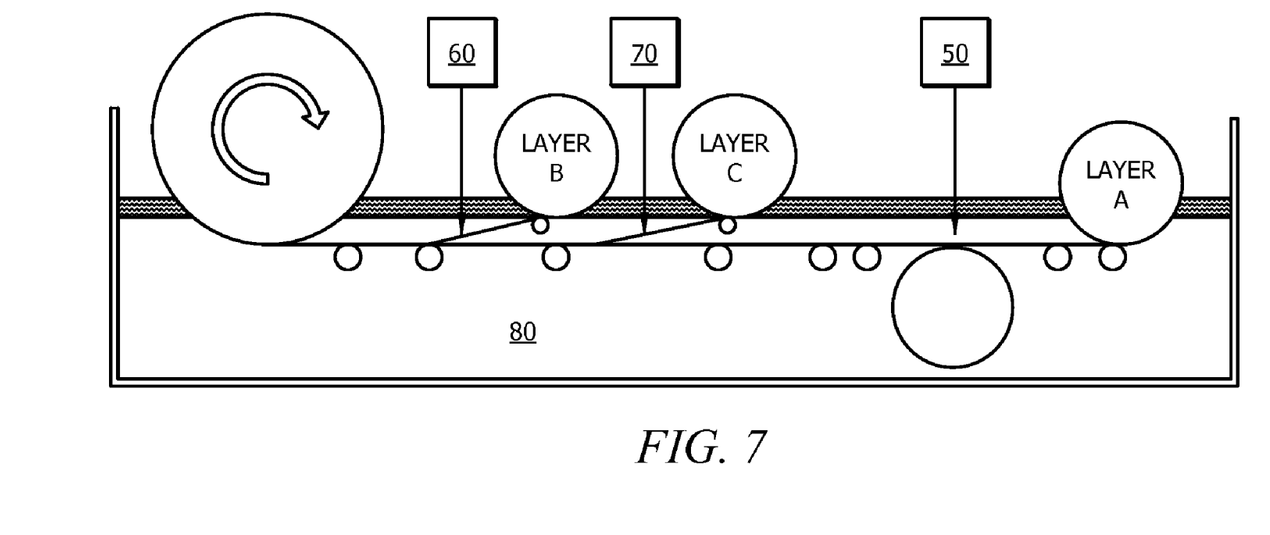
FIG. 7 is a schematic diagram of an assembly system for making multi-layer sheets in accordance with certain embodiments.

In one preferred manufacturing method, several sheet layers are continuously fed from reels, through cell-seeding units onto an assembly wheel, as shown in FIG. 7. In preferred embodiments layer A is assembled first, beginning with hepatocyte placement and patterning at station 50. Next, layers B and C are laid down and each is populated with endothelial cells in the designed portions of its surface at stations 60, 70, respectively. When the multilayer sheet is rolled, its pattern of dividers and openings forms a porous, multilayer structure that mimics that of a natural liver. In order to reduce cell metabolism and prevent cell death or loss of differentiation, the LAD assembly line is preferably immersed in externally oxygenated solution 80 maintained at 4° C. At this low temperature, hepatocytes maintain viability for at least 4 days.

The assembly production speed is limited on the low side by hepatocyte viability in hypoxic environment and on the high side scaffold mechanical strength and by the speed of cell patterning onto the substrate. Taking, as an example, the assembly time per of 4 hours per device, the reeling speed is about 8 mm/s, requiring placement of about 1.5 million cells per second onto a moving substrate.

Cells may be placed onto the substrate by such established techniques as electrophoresis or dielectrophoresis, or new techniques such as microprinting with a stamp, ink jet printing, or optical (laser) tweezers. Contact time should be sufficient to allow the desired number of cells to adhere to the surface.

Variations or Other Embodiments

A primary application for the invention is the manufacture of cellular scaffolds for Extra- or Intra-Corporeal Liver Assist Devices (LADs), also known as Bioartificial Liver, and the assembly of said devices.

An alternative application is as a scaffold in other cellular dialysis devices such as Artificial Kidneys. Benefits of the invention include: extended device performance through use of supporting biomimetic cell arrangement (whether single- or multi-layer), achieved through a biomimetic flow pattern over a large surface area, ease of production as a result of scaffold assembly and cell population process, and compact design, possibly increasing patient mobility.

A second alternative application is as a high surface area membrane such as Artificial Kidney or in other filtration or catalytic devices. Worldwide market for dialysis services exceeds $50 billion. In this application, the invention provides the following benefits: reduced device fabrication costs by enabling a fast device assembly process, due to flow manifolding being accomplished while assembling, layered arrangement of various cell types, and separation of two or more flow streams.

A third alternative application is as a scaffold in bioreactors for culturing cells or tissues. Such cultures may be used, for example, for drug manufacture or testing. Here the invention provides the following benefits: long term cell viability through a biomimetic cell arrangement and solution flow pattern over the large surface area to the cells, high bioreactor productivity through a high density cell arrangement, reduction in reactor setup time by fast scaffold assembly and cell population process, ease of arrangement of several cell types, and separation of metabolic products into separate streams.

This invention utilizes existing state of the art biocompatible materials and known techniques for materials patterning. If used to build a bioartificial organ, the invention can be used in conjunction with known techniques for cell isolation, cell storage, coculture of different cell types, and cell stimulation.

The scaffold geometry of the invention, including sheet patterning and roll-up, provide advantages over known devices.

In its the primary application, the invention improves the long-term LAD performance by increasing the hepatocyte viability and supporting the hepatocyte differentiated function. These are accomplished by placing hepatocytes and stromal cells in biomimetic arrangement, by providing large attachment surface area, by protecting hepatocytes from shear forces, and by providing uniform blood flow and diffusion pathways comparable to in-vivo conditions. Hepatocyte viability is also improved through a completely new feature—scaffold for drainage and separation of bile product. The invention also provides compact device design, potentially increasing patient mobility. This is accomplished through higher cell density than in the prior LADs. Higher cell density is achieved by inventing and utilizing the novel technique of patterning-while-assembling. In prior art, the scaffold has to be perfused with cells after assembly. Therefore, large pores and gaps within the scaffold are required to allow cell perfusion. In this invention, pores and gaps are much smaller. In addition, the invention offers a potential to meet the market demand of tens of thousands of LADs per year with several "mass production" assembly lines. The fast assembly is accomplished through the two novel approaches of this invention: first, a fast flow manifolding, while assembling the device and, second, by populating the scaffold with the cells while assembling the device. In contrast, LADs in clinical trials prior to now employ highly laborious and slow assembly methods. Importantly, the invention also provides a potential to reduces the cost of LAD assembly. The invention accomplishes patterning and assembly of LAD in a fast, automated, continuous fashion, in contrast to the laborious discrete methods for assembly of the existing LADs.

Steps Involved

The invention comprises a new flow pattern design for flat substrates and new assembly process of such substrates into 3 dimensional structures with target 3 dimensional fluid flow patterns. The preferred manufacturing steps include:

1. Selecting and mixing of state of the art scaffold materials, which include, but are not limited to biologically derived materials (basal lamina extracts, collagen, other proteins and proteoglycans,), polymers, and composite membrane materials.
2. Forming scaffold layers into continuous sheet, and, optionally, reeling the layers for storage.
3. Applying designed cell placement and flow patterns to scaffold layers using the state of the art techniques, including protein pattering, molecular imprinting, imprint lithography, rolling, laser ablation, plasma etching, photolithography, and other rapid prototyping tools and, optionally, reeling the layers for storage. The patterns formed on scaffold will hold the cells in place and provide flow channels.
4. If cellular component is to be used, selecting, isolating, and preparing the cells for deposition onto the scaffold layers.
5. Unreeling scaffold layers in a suitable solution that can support cell viability during the scaffold assembly process.
6. Placing cells onto scaffolds at a rate commensurate with target production speed, using such state of the art methods as jet printing, electrophoresis, dielectrophoresis, and optical tweezers.
7. Stacking the scaffold layers in target sequence and reeling them for a target 3 dimensional assembly. As preferred in the present invention, the flow patterns on scaffold layers align vertically during reeling so as to form continuous flow channels.

8. Attaching the inlet and outlet tubes to the flow channel openings on the outer diameter of the reeled scaffold, and manifolding the tubes into a larger tube for connection to the body or to other devices.

The foregoing steps may but need not necessarily be performed sequentially. In some cases it may be desirable to perform two or more steps concurrently, or to begin one step before another step is complete.

The pressure drop from the entry to exit of the scaffold is preferably limited, because high pressure may cause separation of layers and leakages of flows between the layers. This pressure limitation may not matter for human organs, which typically have low pressure drops (i.e. 9 mm Hg for human liver). Bioreactors and filtration devices may need higher pressures. The higher pressure rating may, potentially, be accomplished by joining the layers and sealing the flat surfaces on top and bottom of the assembled cylinder and/or increasing the rigidity of scaffold layers. Other considerations include:

1. Non-uniform flow patters within the layers may cause flow shunts and formation of dead zones. This may, potentially, be overcome by adding grooves and ridges to the layer design.
2. The scaffold sheet may break during the winding and assembly processes. Possible corrective actions include decreasing the assembly reeling speed, using stronger materials, locally reinforcing materials, spacing the reels closer or otherwise reducing the tension on materials
3. Cell may be damaged during the reeling process. Possible corrective actions include: deeper compartments for cell placement on scaffold layers, more time available for cell attachment and slower assembly line speed.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

The teachings of the following references are incorporated herein by reference, except to the extent that they are inconsistent with the present disclosure.

REFERENCES

1. N. L. Sussman and J. H. Kelly, Artificial liver support, Clinical Investigative Medicine; 19 (5): 393-399, 1996
2. K. F. Leong, C. M. Cheah, C. K. Chua, Solid freeform fabrication of three-dimensional scaffolds for engineering replacement tissues and organs, Biomaterials, 24, 2363-2378, 2003
3. M. Mrksich et. al., Using microcontact printing to pattern the attachment of mammalian cells to self-assembled monolayers of alkanethiolates on transparent films of gold and silver, Experimental Cell Research, 235, 305-313, 1997
4. M. Ozkan, T. Pisanie, J. Seheel, C. Barlow, S. Esener, and S. N. Bhatia, Electro-Optical Platform for the Manipulation of Live Cells, Langmuir 2003, 19, 1532-1538
5. K. S. Leclerc, Furukawab, F. Miyatab, Y. Sakaic, T. Ushidab, T. Fujiic, Fabrication of microstructures in photosensitive biodegradable polymers for tissue engineering applications, Biomaterials, 2004
6. Y. Sakai et al., Ultraviolet-irradiation-based photofabrication that simultaneously produces a macroporous structure and flow channels using a photoreactive biodegradable polymer and a gas-forming azoamide compound, Biochemical Engineering Journal, 2003
7. T. B. F. Wood.elda, J. Maldaa, J. de Wijnb, F. Peters, J. Riesleb, C. A. van Blitterswijk, Design of porous scaffolds for cartilage tissue engineering using a three-dimensional fiber-deposition technique, Biomaterials, 2004
8. Wei Tan, T. A. Desai, Layer-by-layer microfluidics for biomimetic three dimensional Structures, Biomaterials, 25, 1355-1364, 2004
9. I. Zein, D. W. Hutmacher, K. C. Tan, S. H. Teoh, Fused deposition modeling of novel sca.old architectures for tissue engineering applications, Biomaterials, 23, 1169-1185, 2002
10. E. A. Roth, T. Xu, M. Das, C. Gregory, J. J. Hickman, T. Boland, Inkjet printing for high-throughput cell patterning, Biomaterials, 2004
11. V. Mironov, T. Boland, T. Trusk, G. Forgacs and R. R. Markwald, Organ printing: computer-aided jet-based 3D tissue engineering, Trends in Biotechnology, 21:4, 157-161, 2003
12. G. Vozzi, C. Flaim, A. Ahluwaliaa, S. Bhatia, Fabrication of PLGA scaffolds using soft lithography and microsyringe deposition, Biomaterials, 24, 2533-2540, 2003
13. R. Landcrs, U. Hubner, R. Schmelzeisen, R. Mulhaupt, Rapid prototyping of scaffolds derived from thermoreversible hydrogels and tailored for applications in tissue engineering, Biomaterials, 23, 4437-4447, 2002
14. I Jasmund, A. Bader, Bioreactor Developments for Tissue Engineering Applications by the Example of the Bioartificial Liver, Advances in Biochemical Engineering, 74, 2002
15. J. W. Allen, T. Hassanein, S. N. Bhatia, Advances in Bioartificial Liver Devices, Hepatology, 34, 247-455, 2001
16. E. Leclere, Y. Sakai, T. Fujii, Perfusion culture of fetal human hepatocytes in microfluidic environments, Biochemical Engineering Journal, 2004
17. N. Fausto, J. S. Campbell, The role of hepatocytes and oval cells in liver regeneration and repopulation, Mechanisms of Development, 120, 117-130, 2003
18. E. Laconi, S. Laconi, Principles of hepatocyte repopulation, Cell & Developmental Biology, 13, 433-438, 2002
19. R. R. Mitry, R. D. Hughes, A. Dhawan, Progress in human hepatocytes: isolation, culture & cryopreservation, Cell & Developmental Biology, 13, 463-467, 2002
20. J. A. Barron, B. R. Ringeisen, D. B. Krizman, B. Spargo, Single Cell Seeding for Use in Tissue Engineering via Laser Printing, Chemistry Division, Naval Research Laboratory, Washington, DC 20375
21. P. V. Moghe et al., Culture Matrix Configuration and composition in the maintenance of hepatocyte polarity and function, Biomaterials, 17, 373-383, 1996
22. F. Berthiaume et. al., Effect of extracellular matrix topology on cell structure, function, and physiological responsiveness: hepatocytes cultured in a sandwich configuration, The FASEB Journal, 10, 1474-1483, 1996
23. A. Bader et. al., 3-D Coculture of Hepatic Sinusoidal Cells with Primary Hepatocytes—Design of an Organotypical model, Experimental Cell Research, 226, 223-233, 1996
24. K. Imai et. al., Adhesion between Cells and Extracellular Matrix with Special Reference to Hepatic Stellate Cell Adhesion to Three-dimensional Collagen Fibers, Cell Structure and Function, 25, 329-336, 2000

25. Uchio et al., ASIAO Transactions, 1998, vol. 23, pages 972-977

26. Gerlach et al., Transplantation, 1994, vol. 58, No. 9

What is claimed is:

1. A bio-artificial organ comprising:
   a substrate comprising a roll of substrate material, said roll of substrate material being formed from a sheet rolled to form a plurality of layers, wherein said sheet includes spacers along its length such that at least a first set of parallel chambers is formed when said roll of substrate material is formed and said sheet includes spaced openings through said sheet and along the length of said sheet such that said plurality of layers are in fluid communication with each other through said spaced openings, said parallel chambers being manifolded to a first inlet and a first outlet; and
   a plurality of cells adhered to said substrate.

2. The bio-artificial organ of claim 1, further including at least a second chamber, said second chamber being isolated from said first set of parallel chambers by at least a cell barrier.

3. The bio-artificial organ of claim 2 wherein said second chamber is provided with a second outlet.

4. The bio-artificial organ of claim 1 wherein said roll of substrate material comprises at least 500 layers.

5. The bio-artificial organ of claim 1 wherein said roll of substrate material includes at least first and second layers, said first layer including a first cell type and said second layer including a second cell type.

6. The bio-artificial organ of claim 5 wherein said first and second layers are separately manifolded.

7. The bio-artificial organ of claim 1 wherein said substrate material comprises a polymer.

8. The bio-artificial organ of claim 1 wherein said substrate material comprises a composite of a biodegradable polymer and a nondegradable polymer.

9. The bio-artificial organ of claim 8 wherein said nondegradable polymer comprises silicone or PDMS.

10. The bio-artificial organ of claim 8 wherein said biodegradeable polymer comprises poly-L-lactic acid, poly-L-glycolic acid, or poly(caprolactone).

11. The bio-artificial organ of claim 1 wherein said substrate material is porous.

12. The bio-artificial organ of claim 1 wherein said sheet comprises a multilayer sheet.

13. The bio-artificial organ of claim 1 wherein the cells are selected from a group consisting of hepatocytes, stromal cells, endothelial cells, kidney cells, and Kuppfer cells.

14. The bio-artificial organ of claim 1 wherein the cells are selected from a group consisting of autologous cells, allogenic cells, immortalized cell lines and xenogenic cells.

15. The bio-artificial organ of claim 1 wherein said substrate material is coated with cell adhesion factors.

16. The bio-artificial organ of claim 1 wherein said sheet has a layer thickness T, said spaced openings are a distance P apart along the length of said sheet and said spaced openings have an opening length L and wherein $2*\pi*T \ll L \ll P$.

17. The bio-artificial organ of claim 1 wherein said sheet has a layer thickness T, said spaced openings are a distance P apart along the length of said sheet, and said spaced openings have an opening length L and wherein T, L, P, and the diameter of the roll are such that each opening is sufficiently aligned with the openings in adjacent layers to allow a flow of fluid therethrough.

* * * * *